(12) United States Patent  (10) Patent No.: US 8,723,513 B2
Ahn et al.  (45) Date of Patent: May 13, 2014

(54) EDDY CURRENT PROBE FOR SURFACE INSPECTION AND EDDY CURRENT INSPECTION DEVICE INCLUDING THE SAME

(75) Inventors: Yeon-Shik Ahn, Daejeon (KR); Sang-Gi Park, Daejeon (KR); Doo-Song Gil, Daejeon (KR)

(73) Assignees: Korea Electric Power Corporation, Seoul (KR); Korea East-West Power Co., Ltd., Seoul (KR)

( * ) Notice: Subject to any disclaimer, the term of this patent is extended or adjusted under 35 U.S.C. 154(b) by 270 days.

(21) Appl. No.: 13/194,273

(22) Filed: Jul. 29, 2011

(65) Prior Publication Data

US 2012/0025814 A1    Feb. 2, 2012

(30) Foreign Application Priority Data

Jul. 29, 2010    (KR) ........................ 10-2010-0073623

(51) Int. Cl.
*G01R 33/12* (2006.01)
(52) U.S. Cl.
USPC ........ 324/239; 73/112.01; 324/238; 324/240; 324/242
(58) Field of Classification Search
None
See application file for complete search history.

(56) References Cited

U.S. PATENT DOCUMENTS 6,745,622 B2 * 6/2004 Smith et al. ................ 73/112.01
7,026,811 B2 * 4/2006 Roney et al. .................. 324/242

FOREIGN PATENT DOCUMENTS

JP      11-064311        3/1999
JP      2005337909 A  * 12/2005
KR     2002-0033073     5/2002

OTHER PUBLICATIONS

Machine English translation of Japanese Patent Application Publication to Inventor Takashi Suzuki. JP 2005-337909 A, Dec. 8, 2005. Translation of pp. 2-9 created on Jun. 15, 2013.*
Korean Office Action, w/ English translation thereof, issued in Korean Patent Application No. 10-2010-0073623, dated Oct. 1, 2010.

* cited by examiner

*Primary Examiner* — Melissa Koval
*Assistant Examiner* — Stephen G Armstrong
(74) *Attorney, Agent, or Firm* — McDermott Will & Emery LLP

(57) ABSTRACT

The present invention discloses an eddy current probe and an eddy current inspection device including the eddy current probe for inspection of surface defect of a rotor wheel including a dovetail coupling part in which a hook is formed. The eddy current probe in accordance with an embodiment of the present invention includes: a main body, a contact part coupled to the main body and having a convex part and a concave part formed thereon corresponding to the hook, and an eddy current sensor being coupled to an end part of the convex part of the contact part. Accordingly, the detectability of a defect and the permeation depth can be enhanced, and the inspection procedures can be simplified.

6 Claims, 6 Drawing Sheets

EDDY CURRENT PROBE FOR SURFACE INSPECTION AND EDDY CURRENT INSPECTION DEVICE INCLUDING THE SAME

CROSS-REFERENCE TO RELATED APPLICATIONS

This application claims the benefit of Korean Patent Application No. 10-2010-0073623, filed with the Korean Intellectual Property Office on Jul. 29, 2010, the disclosure of which is incorporated herein by reference in its entirety.

BACKGROUND

1. Technical Field

The present invention is related to an eddy current probe for surface inspection and an eddy current inspection device including the same.

2. Background Art

Not only is a gas turbine operated at the high temperature of 1300 degrees Celsius, frequent stoppage of motion during the peak season of summer, when power consumption is dramatically increased, causes surface defects to occur in its rotor due to thermal fatigue.

For a magnetic substance gas turbine, defects beyond a certain depth are difficult to be detected by a magnetic particle test because the current density is concentrated on the surface of the rotor due to the high magnetic permeability, and resolution is low for proximate defects, making it difficult to test and evaluate the surface defect of the rotor.

Accordingly, in the case of a magnetic substance rotor, the presence of defects is checked first through a magnetic particle test, and then if a defect is found, the size of the defect is evaluated through an ultrasonic test.

In addition, there have been demands for improvement in non-destructive inspection because harmful materials for humans and environment are generated due to the magnetic powder used in the magnetic particle test and the couplant used in the ultrasonic test.

The only known quantitative non-destructive inspection method for surface defect is the eddy current test (ECT). Accordingly, there is a strong demand for development and application of an eddy current probe that has excellent resolution and enhanced permeation depth in a magnetic substance.

SUMMARY

The present invention provides an eddy current probe and an eddy current inspection device including the eddy current probe that can have excellent detection of defect and have enhanced permeation depth in a magnetic substance.

Moreover, the present invention also provides an eddy current probe and an eddy current inspection device including the eddy current probe that can simplify an inspection process.

Furthermore, the present invention provides an eddy current probe and an eddy current inspection device including the eddy current probe that can prevent harmful materials for humans and environment from being generated due to magnetic powder used in a magnetic particle test or couplant used in an ultrasonic test.

An aspect of the present invention features an eddy current probe for inspection of surface defect of a rotor wheel that includes a dovetail coupling part in which a hook is formed. The eddy current probe in accordance with an embodiment of the present invention can include: a main body; a contact part coupled to the main body and having a convex part and a concave part formed thereon corresponding to the hook; and an eddy current sensor being coupled to an end part of the convex part of the contact part.

The contact part can be removably coupled to the main body.

The eddy current probe in accordance with an embodiment of the present invention can also include: a pressing part configured to press an upper face of the dovetail coupling part; and a first elastic member interposed between the pressing part and the main body and configured to provide elastic force to the pressing part.

The eddy current probe in accordance with an embodiment of the present invention can also include: a rod having one end thereof hinge-coupled to the contact part and the other end thereof formed with a tooth corresponding to the hook of the dovetail coupling part; and a second elastic member interposed between the other end of the rod and the contact part.

Another aspect of the present invention features an eddy current inspection device for inspection of surface defect of a rotor wheel that includes a dovetail coupling part in which a hook is formed. The eddy current inspection device in accordance with an embodiment of the present invention can include: an eddy current probe, which includes a main body, a contact part coupled to the main body and having a convex part and a concave part formed thereon corresponding to the hook, and an eddy current sensor being coupled to an end part of the convex part of the contact part; and a detection part electrically coupled to the eddy current probe and configured to receive, evaluate and control a signal outputted from the main body.

The contact part can be removably coupled to the main body.

The eddy current inspection device in accordance with an embodiment of the present invention can also include: a pressing part configured to press an upper face of the dovetail coupling part; and a first elastic member interposed between the pressing part and the main body and configured to provide elastic force to the pressing part.

The eddy current inspection device in accordance with an embodiment of the present invention can also include: a rod having one end thereof hinge-coupled to the contact part and the other end thereof formed with a tooth corresponding to the hook of the dovetail coupling part; and a second elastic member interposed between the other end of the rod and the contact part.

DETAILED DESCRIPTION

Figure 1:
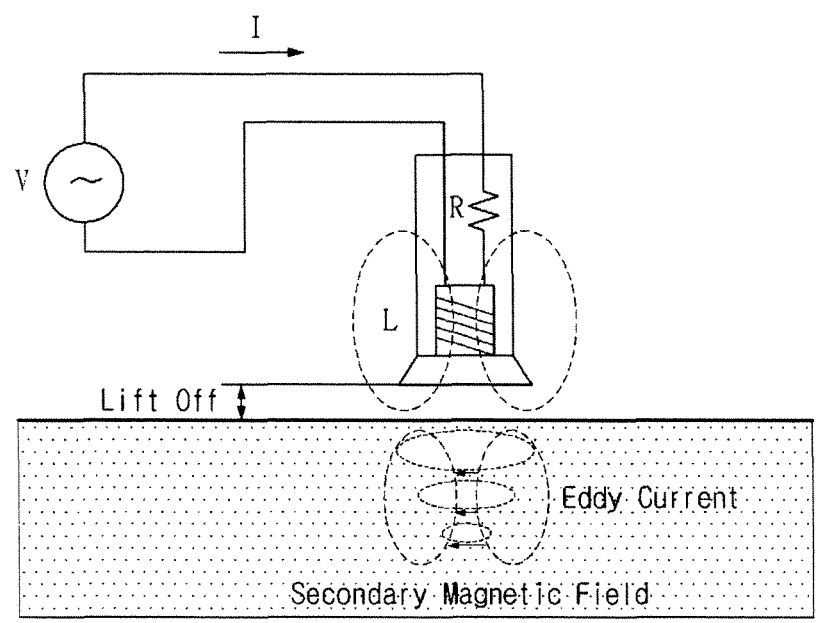
FIG. 1 is a brief diagram illustrating a basic principle of eddy current inspection.

Since there can be a variety of permutations and embodiments of the present invention, certain embodiments will be illustrated and described with reference to the accompanying drawings. This, however, is by no means to restrict the present invention to certain embodiments, and shall be construed as including all permutations, equivalents and substitutes covered by the ideas and scope of the present invention. Throughout the description of the present invention, when describing a certain technology is determined to evade the point of the present invention, the pertinent detailed description will be omitted.

Hereinafter, some embodiments of an eddy current probe for surface inspection and an eddy current inspection device including the same in accordance with the present invention will be described in detail with reference to the accompanying drawings. Identical or corresponding elements will be given the same reference numerals, regardless of the figure number, and any redundant description of the identical or corresponding elements will not be repeated.

Hereinafter, prior to describing an eddy current probe and an eddy current inspection device including the eddy current probe in accordance with certain embodiments of the present invention, the basic principle of eddy current test (ECT) that is applied to the eddy current probe of the present invention will be first described with reference to FIG. 1 in order to help the understanding of the present invention.

FIG. 1 is a brief diagram illustrating the basic principle of eddy current inspection.

Referring to FIG. 1, if an AC current is supplied to a coil, a primary magnetic field is formed around the coil. If the coil forming this primary magnetic field is brought to a conductor, an induced electromotive force is generated inside the conductor by the phenomenon of electromagnetic induction, and this induced electromotive force allows a current that interferes with the primary magnetic field in accordance with Lenz's law. This current is what is referred to as an eddy current. A secondary magnetic field that interferes with the primary magnetic field is formed by the eddy current. The eddy current is altered according to the change in the state, location, defect and material of the conductor, and this alteration of eddy current causes a change in the secondary magnetic field, which then results in a change in the primary magnetic field. The change in the primary magnetic field then results in a change in the impedance of the coil as well as a change in the voltage and phase of a circuit of an inspection device. Accordingly, the change in a circuit value is amplified and outputted as a form in which the shape of a signal can be made out.

Particularly, in implementing an eddy current inspection, magnetic coupling for an object of inspection is a very important factor. The distance between a probe coil and the object of inspection is referred to as a "lift off," which needs to be constant or minimal in order to enhance the sensitivity of inspecting a defect in the object of inspection.

Figure 2:
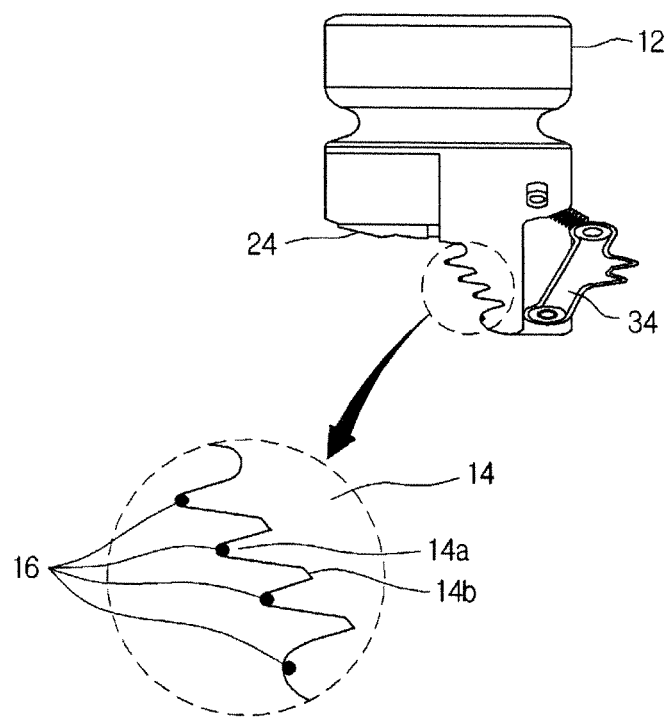
FIG. 2 shows an eddy current probe in accordance with an embodiment of the present invention.
Figure 3:
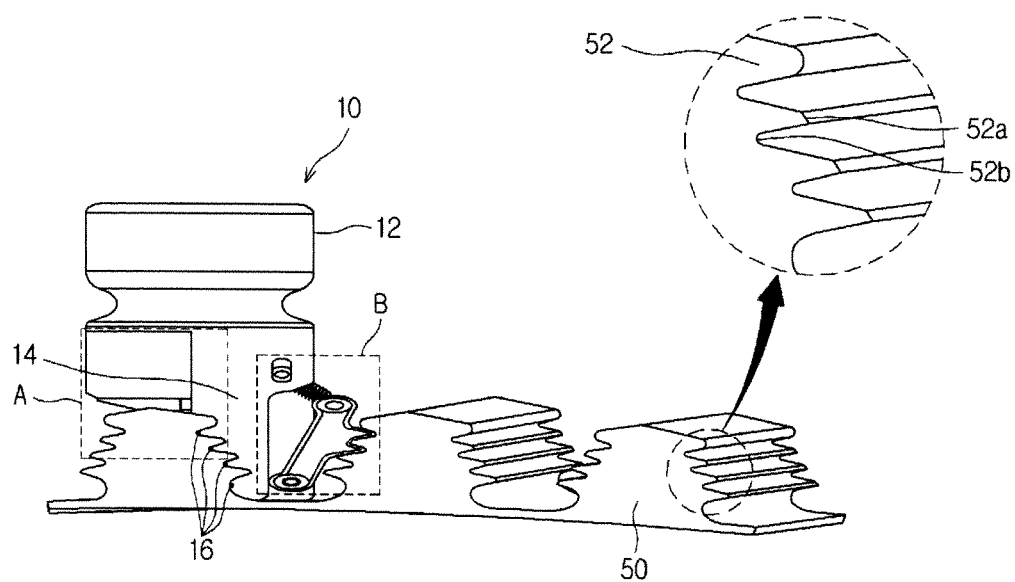
FIG. 3 shows how an eddy current probe in accordance with an embodiment of the present invention is in contact with a dovetail coupling part, which is an object of inspection.

FIG. 2 shows an eddy current probe in accordance with an embodiment of the present invention, and FIG. 3 shows how the eddy current probe in accordance with an embodiment of the present invention is in contact with a dovetail coupling part, which is an object of inspection.

As illustrated in FIG. 2, an eddy current probe 10 for inspection of surface defect of a rotor wheel including a dovetail coupling part 50, in which a hook 52 is formed, in accordance with an embodiment of the present invention can include: a main body 12; a contact part 14 coupled to the main body 12 and having a convex part 14a and a concave part 14b formed thereon corresponding to the hook 12; and an eddy current sensor 16 being coupled to an end part of the convex part 14a of the contact part 14.

The main body 12 has a circuit, etc. installed therein so as to realize the function of the eddy current probe 10, and can be provided with an input/output (not shown) such that the eddy current probe 10 can be electrically connected with an inspection device and a computer.

The contact part 14 is the part that is primarily attached to the dovetail coupling part 50, which is the object of inspection, by forming the convex part 14a and the concave part 14b to correspond to the dovetail coupling part 50, in which the hook 52 is formed. Particularly, unlike the conventional inspection device that mainly inspects an object that has a flat surface, the contact part 14 of the present embodiment is shaped to correspond to the shape of the hook 52 of the dovetail coupling part 50 for close attachment to the hook 52 of the dovetail coupling part 50, for the purpose of enabling surface defect inspection at a convex part 52a and a concave part 52b of the dovetail coupling part 50.

The dovetail coupling part 50 can be provided with different forms depending on the turbine rotor manufacturer. Accordingly, the present embodiment will be described with an assumption that the dovetail coupling part 50 has four hooks.

The eddy current sensor 16 is coupled to the end part of the convex part 14a of the contact part 14 to correspond to the concave part 52b of the dovetail coupling part 50, which is the object of inspection, and functions to detect the defect of the dovetail coupling part 50. The eddy current sensor 16 in accordance with the present embodiment can be coupled to the end part of the convex part 14a of the contact part 14 corresponding to the concave part 52b of the dovetail coupling part 50 so that the end part of the convex part 14a of the contact part 14 is in contact with the concave part 52b of the dovetail coupling part 50, in which defect is most likely to occur. According to the present embodiment, four eddy current sensors 16 can be formed on the convex part 14a of the contact part 14 in order to match with four concave parts 52b formed in correspondence with four hooks 52. Although not illustrated, the eddy current sensor 16 can be coupled to another part, such as the concave part 14b of the contact part 14. Accordingly, surface inspection of another part of the dovetail coupling part 50 is also possible.

Through experiments using stress analysis software, it was discovered that stress is concentrated at the concave part 52b of the dovetail coupling part 50 and that the defect starts occurring at the concave part 52b of the dovetail coupling part 50. In fact, like the result of stress analysis, the defect was concentrated at the concave part 52b of the dovetail coupling part 50. Therefore, in the present embodiment, the eddy current sensor 16 is arranged at a location where the defect is most likely to occur, and the diameter of a coil of the eddy current sensor 16 is designed accordingly.

In the present embodiment, the contact part 14 and the main body 12 are formed in an integrated manner. In this case, several integrated-type eddy current probes, which include the main body 12 and the contact part 14, can be prepared and used in order to inspect surface defect of the dovetail coupling part 50 having different forms depending on the manufacturer. Of course, it is also possible that the contact part 14 is removably coupled to the main body 12. This is to accommodate the dovetail coupling part 50 having different forms depending on the manufacturer, as described above. For this, there can be a plurality of contact parts 14 according to the shape of the hook 52 of the dovetail coupling part 50 that varies depending on the manufacturer, and each contact part 14 can be used by being coupled to the main body 12 as necessary. Here, the contact part 14 and the main body 12 can be electrically connected to each other by, for example, a pin connector (not shown).

Figure 4:
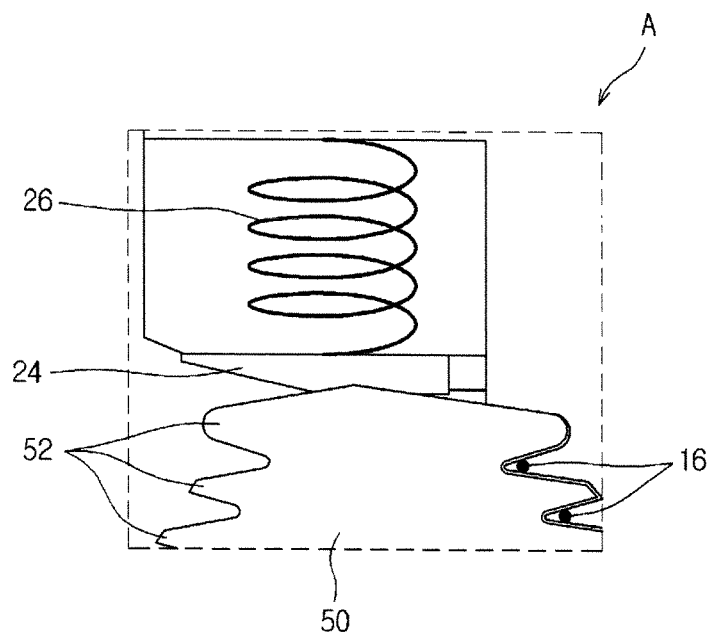
FIG. 4 is an enlarged view of the section marked "A" in FIG. 3.

FIG. 4 is an enlarged view of the section marked "A," with its case removed, in FIG. 3. As illustrated in FIG. 4, the eddy current probe 10 in accordance with the present embodiment can also include a pressing part 24 and a first elastic member 26. Here, the pressing part 24 and the first elastic member 26 can have the form of a pogo pin.

The pressing part 24 functions to facilitate the eddy current sensor 16 and the dovetail coupling part 50, which is the object of inspection, to make contact with each other when the eddy current sensor 16 moves along a direction of inspection, which is a lengthwise direction of the dovetail coupling part 50. For this, the first elastic member 26 can be interposed between the pressing part 24 and the main body 12. In case the height of the dovetail coupling part 50 changes, the pressing part 24 in accordance with the present embodiment can move in the direction of inspection as the pressing part 24 moves up and down along an upper face of the dovetail coupling part 50. Moreover, in case the shape of the upper face of the dovetail coupling part 50 is asymmetric, the pressing part 24 can move in the direction of inspection as the pressing part 24 moves to the left and to the right along the upper face of the dovetail coupling part 50.

As illustrated in FIG. 4, in the present embodiment, the first elastic member 26 can provide elastic force by being interposed between the pressing part 24 and the main body 12 such that the pressing part 24 can press the upper face of the dovetail coupling part 50.

The first elastic member 26 is made of for example, an elastic solid, and elastically supports the pressing part 24 toward the outside in order to transfer the elastic force to the pressing part 24.

As described above, the eddy current probe 10 of the present embodiment can maintain a constant lift off, which is the distance between the eddy current sensor 16 and the object of inspection, by having the pressing part 24 and the first elastic member 26. Also, the eddy current probe 10 of the present embodiment can be inserted in a slot formed between two adjacent dovetail coupling parts 50 and move along the direction of inspection, which is the lengthwise direction of the dovetail coupling part 50.

Figure 5:
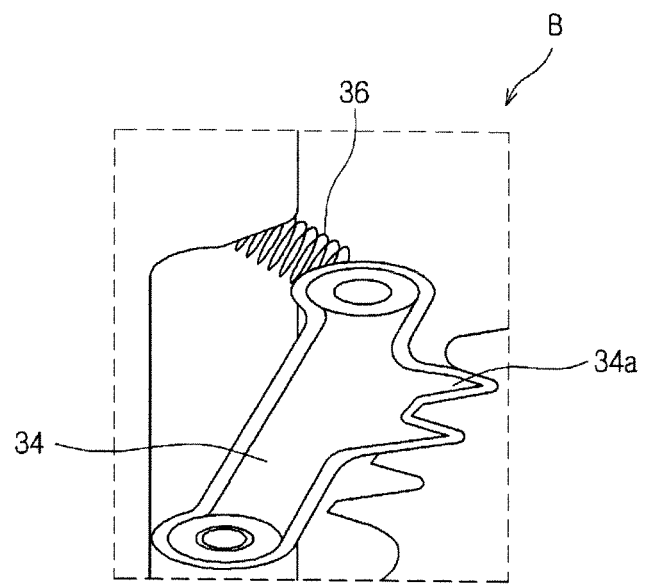
FIG. 5 is an enlarged view of the section marked "B" in FIG. 3.

FIG. 5 is an enlarged view of the section marked "B" in FIG. 3. As illustrated in FIG. 5, the eddy current probe 10 in accordance with the present embodiment can also include a rod 34 and a second elastic member 36.

The rod 34 and the second elastic member 36 function to maintain constant contact pressure between the eddy current sensor 16 and the object of inspection so that a constant space is maintained between the eddy current sensor 16 and the object of inspection. As mentioned earlier, maintaining a constant left off between an eddy current sensor and an object of inspection directly affects the reliability of the result of inspection in an eddy current inspection. Therefore, it is imperative that the lift off is always maintained to be constant or minimal.

For this, in the present embodiment, one end of the rod 34 can be hinge-coupled to the contact part 14, and one side of the rod 34 can be formed with a tooth 34a corresponding to an adjacent hook of the dovetail coupling part 50. Moreover, the second elastic member 36 can be interposed between the other end of the rod 34 and the contact part 14.

The second elastic member 36 is made of, for example, an elastic solid, and elastically supports the rod 34 toward the outside in order to transfer the elastic force to the rod 34.

As described above, the eddy current probe 10 of the present embodiment can enhance the detectability of a defect and the permeation depth, by being coupled to the end part of the convex part 14a of the contact part 14 corresponding to the concave part 52b of the dovetail coupling part 50 such that the eddy current probe 10 is in contact with the concave part 52b of the dovetail coupling part 50, in which defect is most likely to occur. Moreover, unlike the conventional inspection device that mainly inspects an object having a flat surface, surface inspection is possible at the convex part 52a and the concave part 52b of the dovetail coupling part 50, thereby simplifying the inspection procedures.

Furthermore, the eddy current probe 10 of the present embodiment can allow the inspection procedures to be simpler and performed quickly by being inserted in the slot and moving along the direction of inspection.

Figure 6:
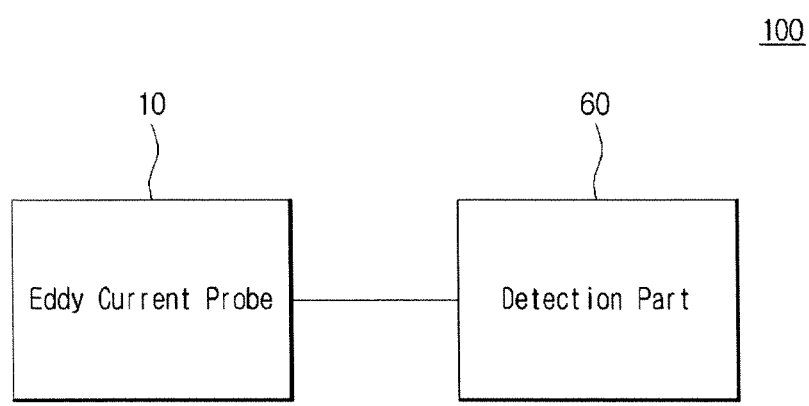
FIG. 6 is a brief configuration of an eddy current inspection device in accordance with an embodiment of the present invention.

FIG. 6 is a brief configuration of an eddy current inspection device in accordance with an embodiment of the present invention. As illustrated in FIG. 6, an eddy current inspection device 100 in accordance with an embodiment of the present invention includes an eddy current probe 10 and a detection part 60.

The eddy current inspection device 100 for inspection of surface defect of a rotor wheel including a dovetail coupling part 50, in which a hook 52 is formed, in accordance with an embodiment of the present invention can include: the eddy current probe 10, which includes a main body 12, a contact part 14 coupled to the main body 12 and having a convex part 14a and a concave part 14b formed thereon corresponding to the hook 52, and an eddy current sensor 16 being coupled to an end part of the convex part 14a of the contact part 14; and the detection part 60 being electrically connected with the eddy current probe 10 and configured to receive, evaluate and control a signal outputted from the main body 12.

In the present embodiment, the configuration and function of the eddy current probe 10 are identical to those of the earlier-described embodiment, and thus no description on the eddy current probe 10 will be provided herein, but the detection part 60 will be described hereinafter.

The detection part 60 can be provided with a plurality of input/output parts such that the detection part 60 can be electrically connected with the main body 12 of the eddy current probe 10 or a computer (not shown), and functions to read, evaluate and control a signal outputted from the main body 12. For instance, the detection part 60 can be TC-5700 of RD Tech., which is a multi-channel device that operates by being connected with a personal computer through a LAN.

As described above, the eddy current inspection device 100 of the present embodiment can enhance the detectability of a defect and the permeation depth, by being coupled to the end part of the convex part 14a of the contact part 14 corresponding to the concave part 52b of the dovetail coupling part 50 such that the eddy current probe 10 is in contact with the concave part 52b of the dovetail coupling part 50, in which defect is most likely to occur. Moreover, unlike the conventional inspection device that mainly inspects an object having a flat surface, surface inspection is possible at the convex part 52a and the concave part 52b of the dovetail coupling part 50, thereby simplifying the inspection procedures.

The eddy current probe and the eddy current inspection device including the eddy current probe in accordance with the present invention do not use the magnetic particle test or ultrasonic test, and thus materials harmful to the humans and environment can be prevented from being generated due to the magnetic powder used in the magnetic particle test or the couplant used in the ultrasonic test.

Although some embodiments of the present invention have been described, it shall be appreciated that there can be a very large number of permutations and modification of the present invention by those who are ordinarily skilled in the art to which the present invention pertains without departing from the technical ideas and boundaries of the present invention, which shall be defined by the claims appended below.

It shall be also appreciated that many other embodiments other than the embodiments described above are included in the claims of the present invention.

What is claimed is:

1. An eddy current probe for inspection of a surface defect of a rotor wheel that includes a dovetail coupling part in which a hook is formed, the eddy current probe comprising:
    a main body;
    a contact part coupled to the main body and having a convex part and a concave part formed thereon corresponding to the hook;
    an eddy current sensor being coupled to an end part of the convex part of the contact part;
    a pressing part configured to press a top surface of the dovetail coupling part; and
    a first elastic member interposed between the pressing part and the main body and configured to provide elastic force to the pressing part, wherein
    the pressing part is arranged to move up and down along the top surface of the dovetail coupling part.

2. The eddy current probe of claim 1, wherein the contact part is removably coupled to the main body.

3. The eddy current probe of claim further comprising:
    a rod having one end thereof hinge-coupled to the contact part and the other end thereof formed with a tooth corresponding to the hook of the dovetail coupling part; and
    a second elastic member interposed between the other end of the rod and the contact part.

4. An eddy current inspection device for inspection of a surface defect of a rotor wheel that includes a dovetail coupling part in which a hook is formed, the eddy current inspection device comprising:
    an eddy current probe comprising a main body, a contact part coupled to the main body and having a convex part and a concave part formed thereon corresponding to the hook, and an eddy current sensor being coupled to an end part of the convex part of the contact part;
    a detection part electrically coupled to the eddy current probe and configured to receive, evaluate and control a signal outputted from the main body;
    a pressing part configured to press a top surface of the dovetail coupling part; and
    a first elastic member interposed between the pressing part and the main body and configured to provide elastic force to the pressing part, wherein
    the pressing part is arranged to move up and down along the top surface of the dovetail coupling part.

5. The eddy current inspection device of claim 4, wherein the contact part is removably coupled to the main body.

6. The eddy current inspection device of claim 4, further comprising:
    a rod having one end thereof hinge-coupled to the contact part and the other end thereof formed with a tooth corresponding to the hook of the dovetail coupling part; and
    a second elastic member interposed between the other end of the rod and the contact part.

* * * * *